United States Patent [19]

Min et al.

[11] Patent Number: 5,797,932

[45] Date of Patent: Aug. 25, 1998

[54] MUSCLE CLAMPING DEVICE

[75] Inventors: Byung-Moo Min; Joon Mook Yang; Nam Sook Cho, all of Daejon, Rep. of Korea

[73] Assignee: Jong-Deok Park, Daejon, Rep. of Korea

[21] Appl. No.: 637,458

[22] Filed: Apr. 25, 1996

(Under 37 CFR 1.47)

[51] Int. Cl.$^6$ .................................................. A61B 17/08
[52] U.S. Cl. ...................... 606/151; 606/157; 606/148; 606/232
[58] Field of Search ........................... 606/151, 157, 606/158, 220, 148

[56] References Cited

U.S. PATENT DOCUMENTS

| 4,060,089 | 11/1977 | Noiles | 606/220 |
| 5,275,578 | 1/1994 | Adams | 606/151 |

FOREIGN PATENT DOCUMENTS

| 130037 | 2/1985 | European Pat. Off. | 606/220 |

*Primary Examiner*—Michael Buiz
*Assistant Examiner*—Daphna Shai
*Attorney, Agent, or Firm*—Dann, Dorfman, Herrell and Skillman; Henry H. Skillman

[57] ABSTRACT

A bioabsorbable clamping apparatus for using in extraocular muscle surgery, for example, for curing strabismus is disclosed. The invention consists of two embodiments to be joined together. In one embodiment, a fixing means comprises two opposing bodies to be interlocked such as an upper fixing body and a lower fixing body. In another embodiment, a supporting body comprises two bodies, posteriorly connected along with above said bodies, such as the upper supporting body upholding and fastening the said upper fixing body, and a lower supporting body upholding and fastening the said lower fixing body. This invention provides for the muscle clamping apparatus wherein the said lower fixing body passes through the muscle to thereby cause the muscle to be connected together with the said upper fixing body when forcibly engaged to each other and to the said supporting body.

7 Claims, 7 Drawing Sheets

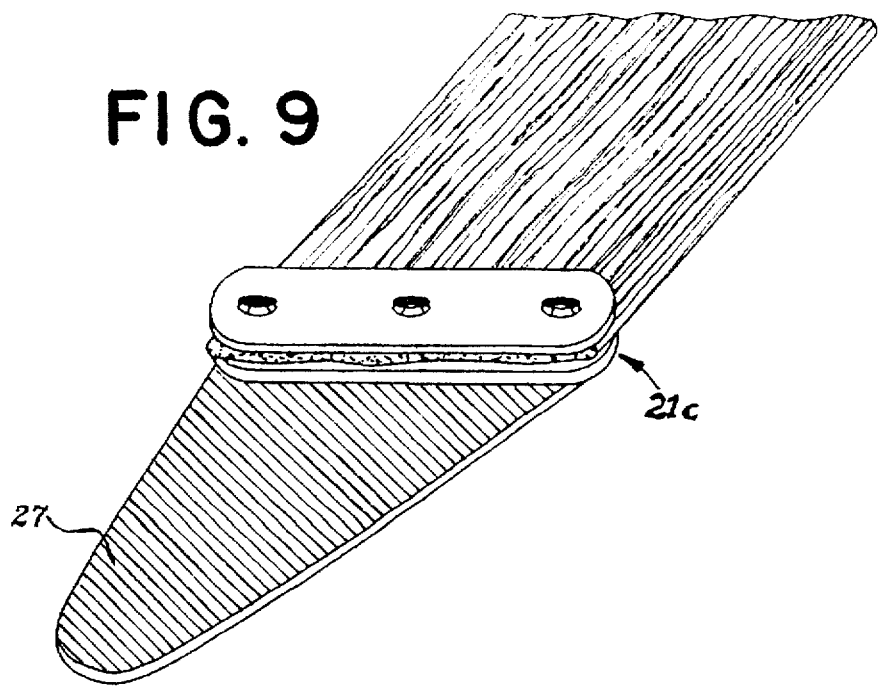
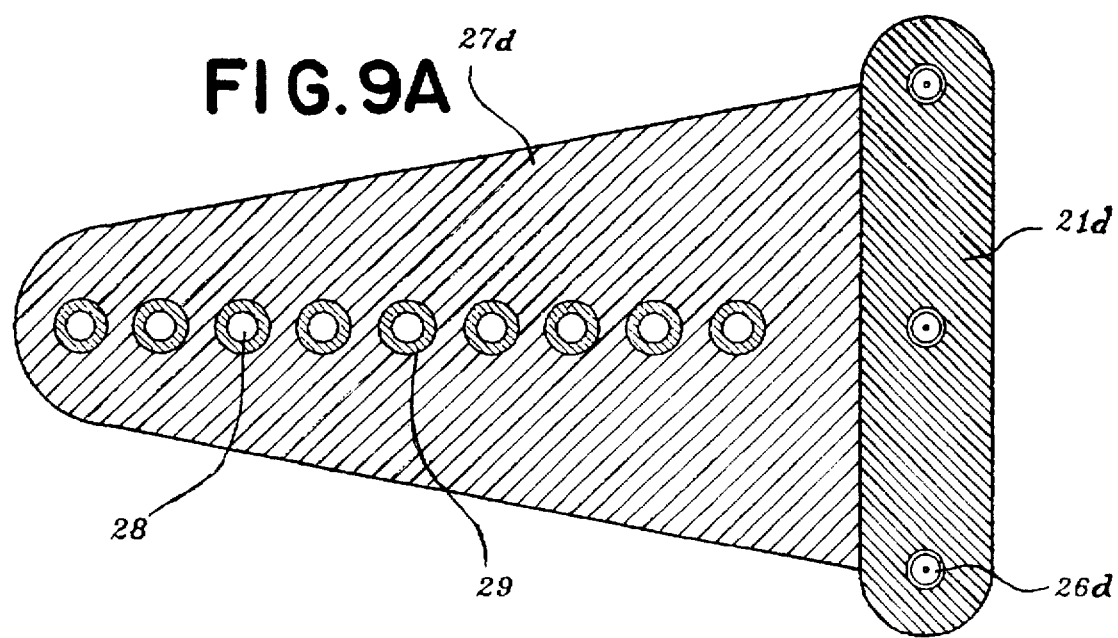

MUSCLE CLAMPING DEVICE

FIELD OF THE INVENTION

This invention relates generally to a clamping apparatus for muscle more specifically, this invention relates to a bioabsorbable clamping apparatus for using in extraocular muscle surgery, for example, for curing strabismus.

BACKGROUND OF THE INVENTION

The conventional method for strabismus surgery requires suture (and needle) 1, as illustrated in FIGS. 1A and 1B to be weaved in (and out of the extra ocular muscle 2, while passing the needle) through the sclera 3(the tough coat of the eye) and thereby fixing the muscle 2 to the sclera 3.

This method brings about potential complications. To begin with, the suture binding the muscle 2 may get so loose that strabismus surgery may be performed incorrect; whose result may suggest the case of resurgery. Then, endophthalmitis may occur in penetrating the sclera when the needle goes through it, which is only 0.3 mm thick; and penetration may be either too deep or too shallow. And serious complications may occur such as separation of the retina, partial death necrosis of the retina, anterior hemorrhage, dislocation of the lens, and even blindness and loss of the eyeball.

Conventionally, the type of the hang-loose has been employed to solve such problems. In accordance with FIGS. 2A and 2B, this is accomplished first binding the extraocular muscle 2 by suture and needle 1, but not passing the needle through the sclera 3; then hanging loose the muscular portion attached to the muscle 2; and finally cutting off this portion, which is posteriorly to be resecured further back by means of suture.

The hang-loose has such a disadvantage that it makes narrow the muscular width of the extraocular muscle 2, depending on stretching the suture 1; whereby the movement of the ocular muscle will become unstable after it is resecured.

For this case, Lingua in the U.S. Pat. No. 4,519,392 as of May 28, 1985 shows a type of operation by using a clip, not binding the ocular muscle by suture, entitled "Hemostasing Muscle Clips for Needleless Surgery", as illustrated in FIG. 3. According to this type, two clips 7 and 7' are to clamp each side of the ocular muscle; then, the muscle between the two clips are cut off; and the length of the suture 8 comes to be adjusted according to its amount as needed, so that after fixing its two ends to the holes 9 and 9' of each clip, it is pulled backward.

This way of operation appears complicated not only in the method for two clips to clip the ocular muscle, but also in the method for manipulating two parallel sutures to thereby stretch them out to the same length as needed. So it become not utilized due to complexities and difficulties.

SUMMARY OF THE INVENTION

The purpose of the invention is to provide for a clamping apparatus capable of clipping the muscle, for example, the ocular muscle with ease by simple manipulation.

For this, the invention consists of two embodiments to the joined together. In one embodiment, a fixing means comprises two opposing bodies to be interlocked such as an upper fixing body and a lower fixing body. In another embodiment, a supporting body comprises two bodies, posteriorly connected along with above said bodies, such as the upper supporting body upholding and fastening the said upper fixing body, and a lower supporting body upholding and fastening the said lower fixing body. This invention provides for the muscle clamping apparatus wherein the said lower fixing body passes the muscle to thereby be connected together with the said upper fixing body when are given force out of the outer side of the said supporting body.

BRIEF DESCRIPTION OF THE DRAWINGS

FIG. 9 is an perspective view using a variation of the lower fixing body having a membrane in accordance with this invention.

FIG. 9A is a top view of another variation of the membrane of the lower fixing body.

DETAILED DESCRIPTION OF THE INVENTION

In accordance with this invention, the apparatus consists of the fixing means to fasten the muscle, and the supporting means, shaped like pincettes to forcibly engage the fixing means, in order for the said fixing means to fasten the muscle. The fixing means comprises a lower fixing body and an upper fixing body, and the supporting means comprises a lower supporting body and an upper supporting body. The fixing means is made of bioabsorbable material like polymer, and the supporting means is made of material like metal.

Figure 1A:
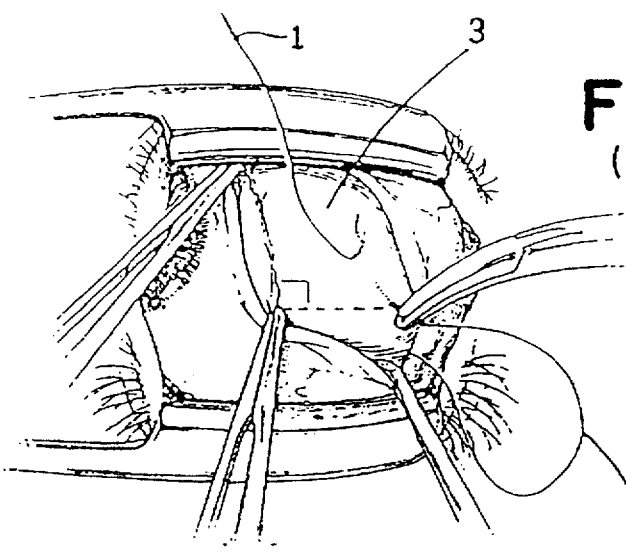
FIGS. 1A and 1B illustrate one method of operation by old techniques.
Figure 1B:
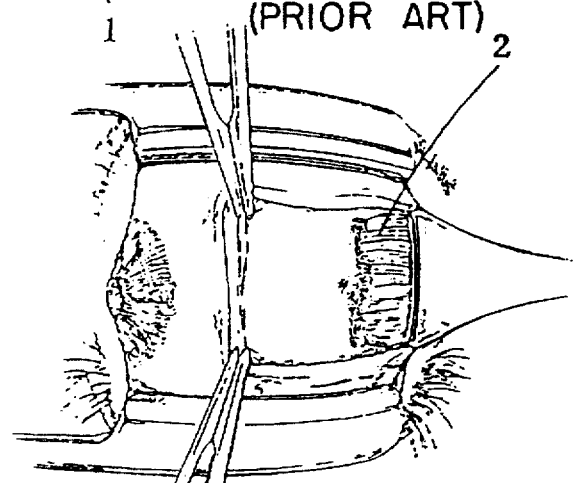
Figure 2B:
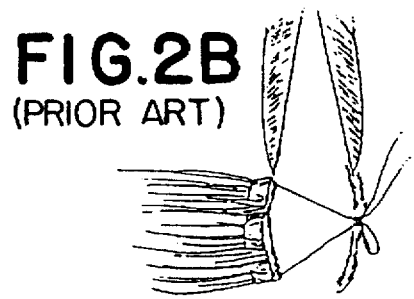
FIGS. 2A and 2B illustrate another method of operation by old techniques.
Figure 2A:
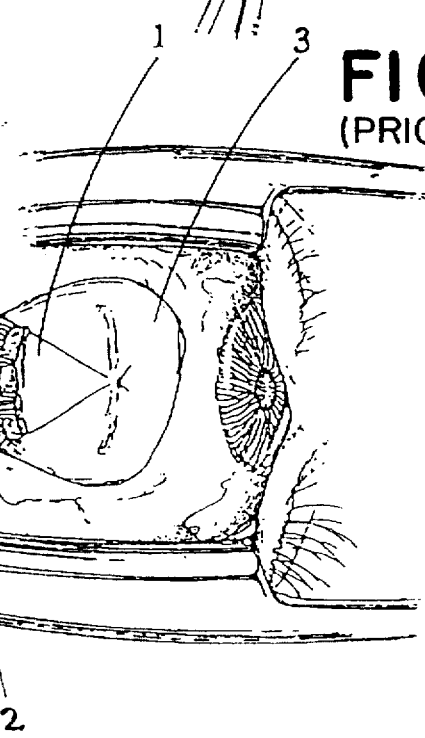
Figure 3:
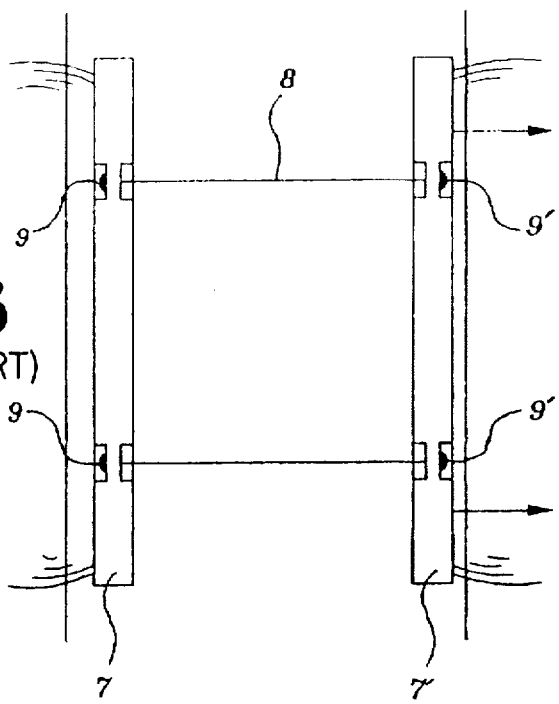
FIG. 3 illustrates the prior art clips used for operation by old techniques.
Figure 4A:
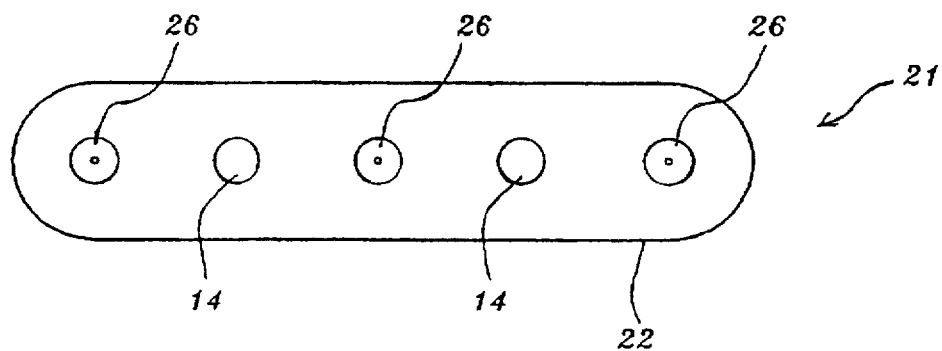
FIGS. 4A and 4B are top and cross-sectional views respectively of the lower fixing body in accordance with an embodiment of the present invention.
Figure 4B:
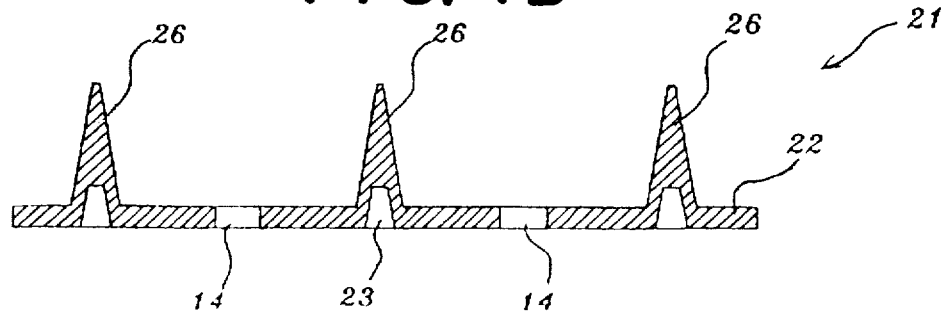

Referring to FIG. 4A and 4B there is shown an illustration of an embodiment of the lower fixing body, according to the present invention. The lower fixing body 21 consists of the base part 22 where the penetrating holes 14 for inserting suture are set up at preset positions, and the projecting parts 26, tapered in shape, protrude from one surface of the base part. The base part 12 is has 0.08–0.15 mm thick in general. The top of the tapering projecting parts 26 has an acute angle to the degree capable of piercing the muscle, and in the opposite surface of the base part in registry with the projection parts, the groove part 23 is made having a taper angle equivalent or akin to it. In either way, the said projecting parts 26 can be formed in a single body of the base part 22, as shown; or and the projecting parts 26 having the said groove 23 can be made separately to attach.

Figure 4D:
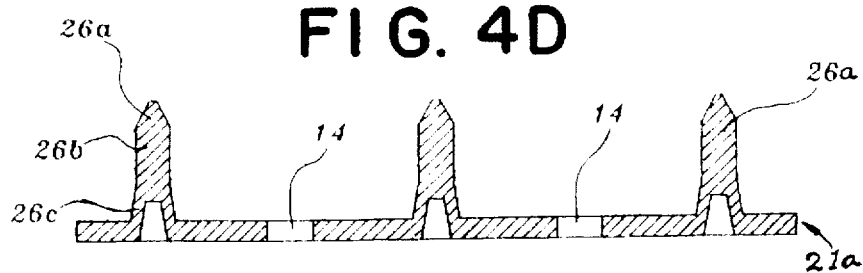
FIGS. 4C and 4D are top and cross-sectional views respectively of the lower fixing body in accordance with another embodiment of the present invention.
Figure 4C:
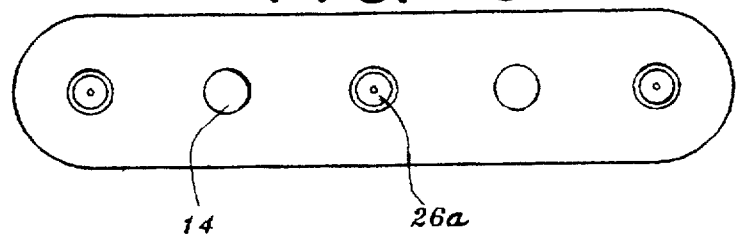

FIGS. 4C and 4D illustrate another embodiment of the lower fixing body of the invention. Unlike the first embodiment, the projecting parts consist of three sections different in body 21a such as a top portion 26a, a middle portion 26b, and a bottom portion 26c. The top portion 26a has an acute angle; the middle one 26b forms a cylinder of same diameter in set distance; the bottom one 26c is in taper body.

Figure 5A:
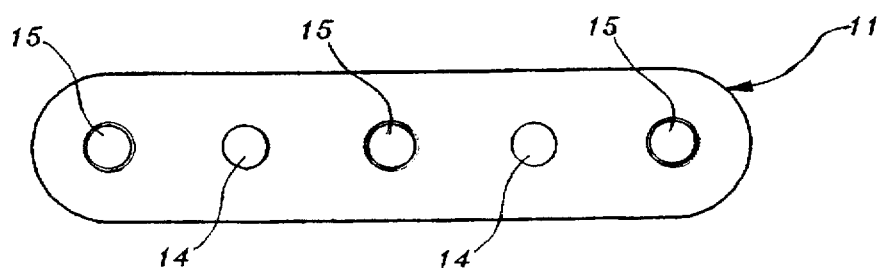
FIGS. 5A and 5B are top and cross-sectional views respectively of the upper fixing body in accordance with the present invention.
Figure 5B:
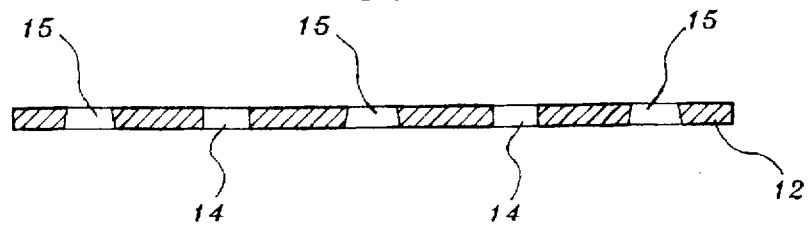

FIGS. 5A and 5B illustrate an embodiment of the upper fixing body, in this invention. The upper fixing body 11 consists of the base part 12 wherein a plurality of penetrating holes 14,15 are made. The base part 12 is 0.08–0.15 mm thick in general, referring to the range where the base part 12 itself will not be ripped and the penetrating holes 15 for connection, which serve as receptacles for the projecting parts 26, can be transformed with ease when the projecting part of the said lower fixing body gets inserted into the penetrating hole. In this embodiment, the form of the base part is generally rectangular, each end of which is shaped in circular arc, but as mentioned later, it can vary as far as it corresponds to the recess structure of the upper supporting body shown in FIGS. 6A and 6B.

Each of the penetrating holes 14 for inserting suture is situated opposite to so as to register with each of the penetrating holes for inserting suture of the lower fixing body, and each of the penetrating hole 15 for connection is situated opposite to each of the projecting parts 26 of the lower fixing body.

The inner side of the penetrating hole 15 for connection formed to register with to the projecting parts 26 is preferably tapered equivalent to the taper angle of the projecting part.

Also, the diameter of the penetrating hole 15 can vary depending on the thickness of the muscle. Generally in the lower fixing body as illustrated in an embodiment of the invention, the said diameter is designed to be equal to that of a certain middle level of the tapered projecting part 26. In the lower fixing body as illustrated in another embodiment, the said diameter is designed to be equivalent to that of the middle portion 26b of the projecting part 26.

The projecting part 26 and the penetrating hole 15 for connection are joined together in mutually tapered states; wherein a taper angle can be accepted if it satisfies a self-locking conditions, as can secure in a set position without getting loose by itself. That is, when α taper angle is α, it can he accepted to satisfy the following:

$$\alpha \leq \rho$$

Here, ρ signifies a friction angle depending on the nature of material of which the projecting part and the upper fixing body are made.

Also, the penetrating hole for inserting suture of the upper fixing body 14 and that of the lower fixing body 24 need not have identical diameters; their diameters can be accepted simply if the center line of the penetrating holes register enough for suture to pass through.

On the other hand, the supporting body is an apparatus for applying force in order for the upper and lower fixing bodies to be able to clamp the muscle squeezed between them, the support comprising the upper supporting body, the lower supporting body, and the connecting part which has not been in FIGS. 6 and 7 Accordingly in total, the supporting body looks like pincettes, and the illustration of the connecting part is omitted because it seems not to belong to the major element of this invention.

Figure 6B:
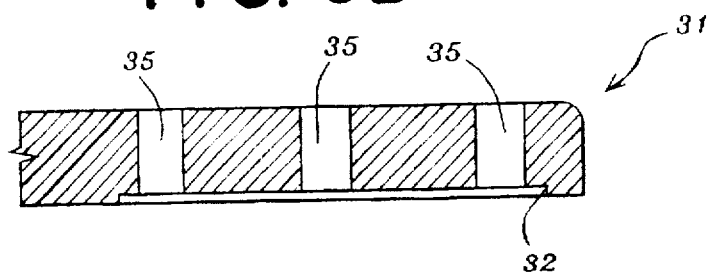
FIGS. 6A and 6B are fragmentary bottom and cross-sectional views respectively of the upper supporting body in accordance with the present invention.
Figure 6A:
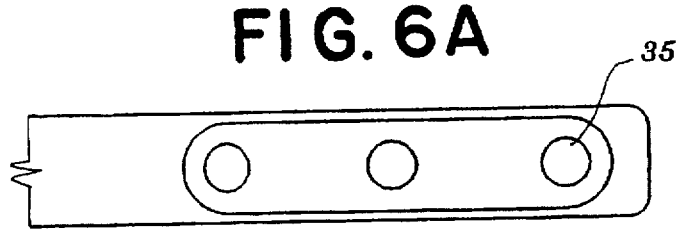

FIG. 6B is a cross-sectional view of the upper supporting body and FIG. 6A is plan view, as illustrated in an embodiment of the invention. On the bottom surface of the upper supporting body 31, the recess portion 32 is formed to interlock the upper fixing body, and the penetrating holes 35 are formed to receive the projecting parts of the lower fixing body. The recess portion 32 is formed at the same height of the upper fixing body 11, so that its bottom side gets leveled when the upper fixing body is inserted. Also, the width and area of the recess portion are a little less than the upper fixing body, or they are made equivalent to those of the upper fixing body, to the extent that the upper fixing body won't escape from the supporting body by frictional force when one is put into the other.

The diameter of the penetrating hole 35 is made either equivalent to, or a little bigger than, that of the bottom portion of the tapered projecting part 26 of the lower fixing body 21, in order to be able to receive the whole projecting part of the lower fixing body.

Figure 7B:
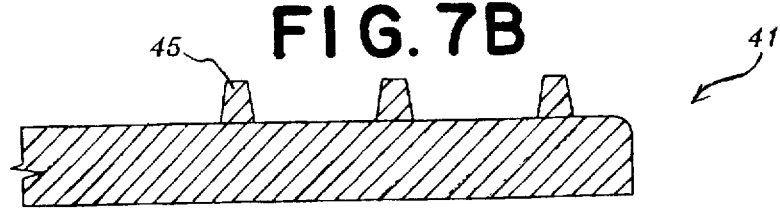
FIGS. 7A and 7B are fragmentary top and cross-sectional views respectively of the lower supporting body in accordance with an embodiment of the present invention.
Figure 7A:
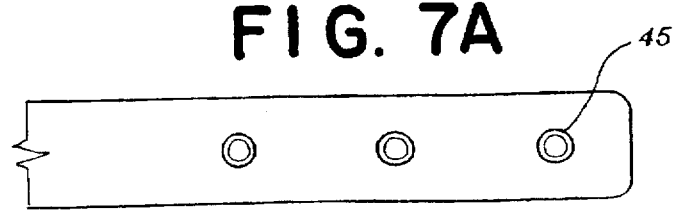

Referring to FIG. 7A and 7B there is shown an embodiment of the lower supporting body of the invention.

In the upper portion of the lower supporting body 41, there is a supporting part 45 in projected form, opposite to the penetrating hole for connection of the lower fixing body 21, and designed to be inserted into its groove part 23, to thereby uphold the lower fixing body. In this embodiment, the said supporting part 45 is tapered, making its diameter, according to its height, either a little bigger than, or equivalent to, that of the said groove part 23, to thereby secure the lower fixing body 21 by frictional force when they are interlocked.

Figure 7C:
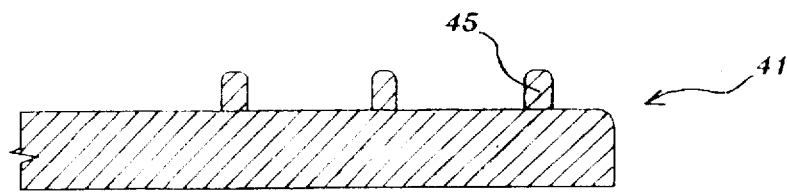
FIG. 7C is a fragmentary cross-sectional view of the lower supporting body in accordance with another embodiment of the present invention.

FIG. 7C shows an another embodiment of the supporting part. The shape and height(depth) of the said supporting part do not suggest any problem if it can certainly secure the lower fixing body 21 as being inserted into the lower supporting body 41 whereby to connect the groove part 23.

The following will explain the method of surgery, for example, for the ocular muscle, by employing this invention, as illustrated in FIG. 8.

Figure 8A:
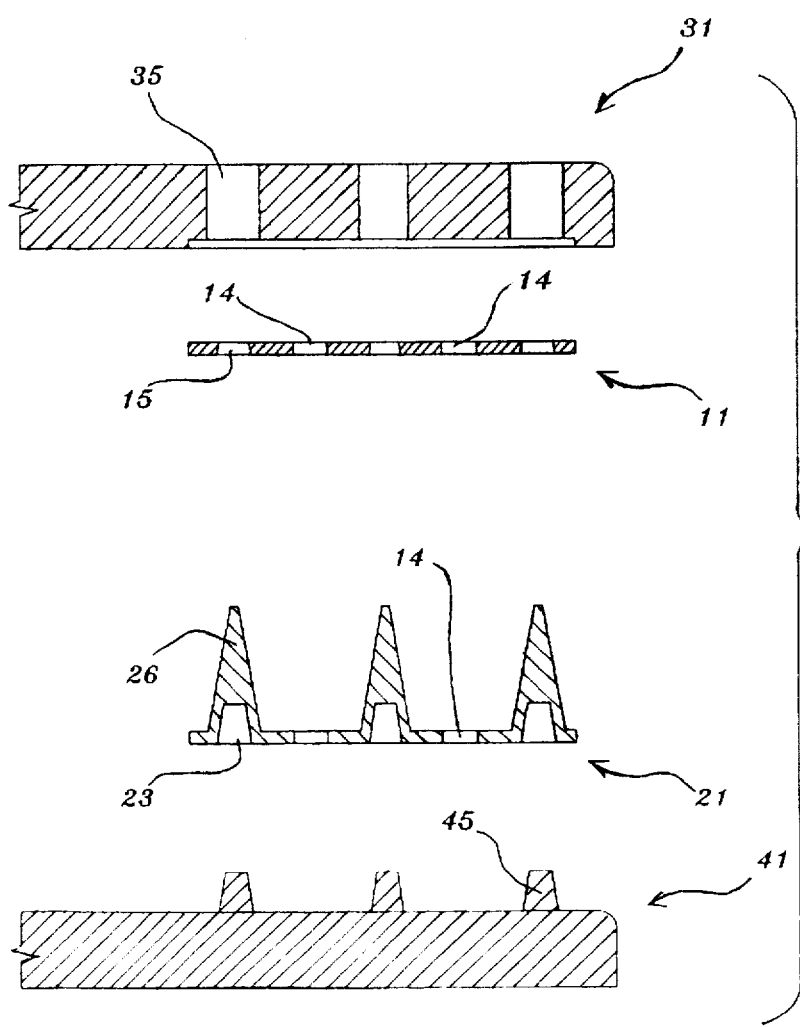
FIG. 8A is a fragmentary exploded view illustrating connecting the fixing means with the supporting means.

To begin with as illustrated in FIG. 8A, the groove part 23 of the lower fixing body 21 is put into the supporting part 45 of the lower supporting body 41, and then the upper fixing body 11 is put into the recess part 32 of the upper supporting body 31. Then, the groove part 23 of the lower fixing body has the same taper angle as the support part 45 of the lower supporting body, and they are secured to uphold each other by frictional force because the diameter of the former is either a little bigger than, or equivalent to, that of the latter, in accordance with the height of the said supporting part 45. Also, the upper fixing body is interlocked with the recess part 32 of the upper supporting body once they are interlocked, one is hardly detached from the other by the frictional force produced out of a mutual contact between the platform-elevated part 32 of the upper supporting body, and the upper fixing body, because the size of the upper fixing body is either bigger than, or equivalent to, that of the recess part In this state, the ocular muscle 50 is put between the upper and lower fixing parts. Then, either following procedures will be used: one way is that the muscle is cut in advance, and it is thereby put between the upper and lower fixing bodies; the other way is that the muscle is not cut, after the muscle is raised up, once the upper and lower supporting bodies, in each of which the upper and lower fixing bodies are inserted, are put together on the opposite upper and lower sides of the muscle.

Figure 8B:
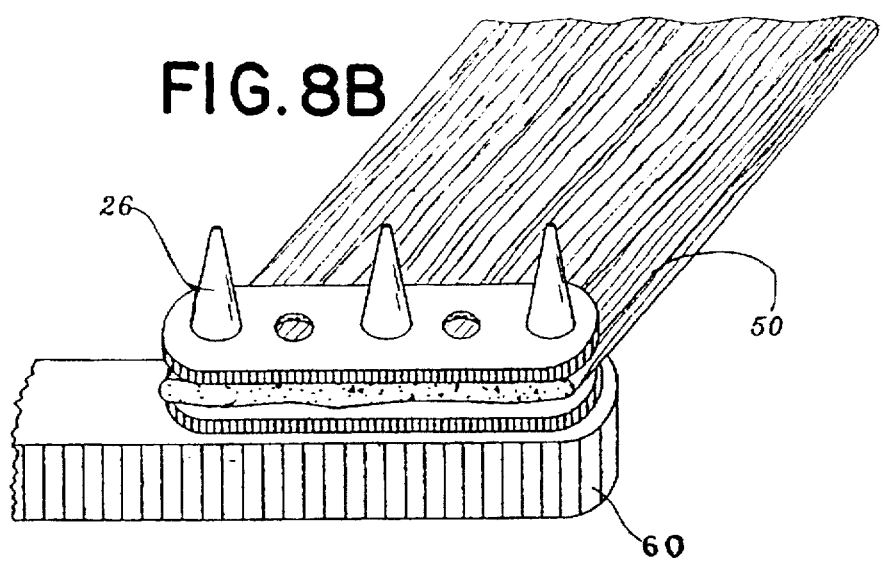
FIG. 8B is a view illustrating the assembly after the lower fixing body pierces the muscle by applying force to the supporting means.

FIG. 8B illustrates the state of detaching the upper supporting body from the upper fixing body after the upper and lower supporting bodies are forced together using a connecting part 60.

The ocular muscle is put between the upper and lower fixing bodies. As the upper and lower fixing bodies are forced together, the upper portion, shaped in an acute angle, of the projecting parts 26 of the lower fixing body pierces the muscle, and then it passes through the penetrating hole 15 for connection of the upper fixing body and the penetrating hole 35 of the upper supporting body.

Here, the length of the projecting parts of the lower fixing body which is protruded through the penetrating holes 15 for connection of the upper fixing body may vary depending on the thickness of the muscle inserted. For example, if the thickness of the muscle is assumed to be the half level of the projecting part of the lower fixing body, the diameter of the penetrating hole 15 for connection of the upper fixing body can be set up equivalent to the diameter in the height of about half level of the projecting part 26 of the lower fixing body.

Then, as the projecting part 26 and the penetrating hole 15 of the upper fixing body have the same taper angle and they are forced to be connected by outer force, they won't get loose by frictional force. In this state, as the upper and lower supporting bodies are detached, the penetrating hole 15 is hardly in touch with the projecting part because the diameter of the former 15 is either equivalent to, or bigger than, that of the bottom of the latter. And since the frictional force between the projecting part 26 and the penetrating hole 15 for connection of the upper fixing body is much bigger than the frictional force between the recess part 32 of the upper supporting body and the upper fixing body, the upper supporting body only is detached with ease while the upper and lower fixing bodies hold the muscle, as illustrated in FIG. 8B.

Figure 8C:
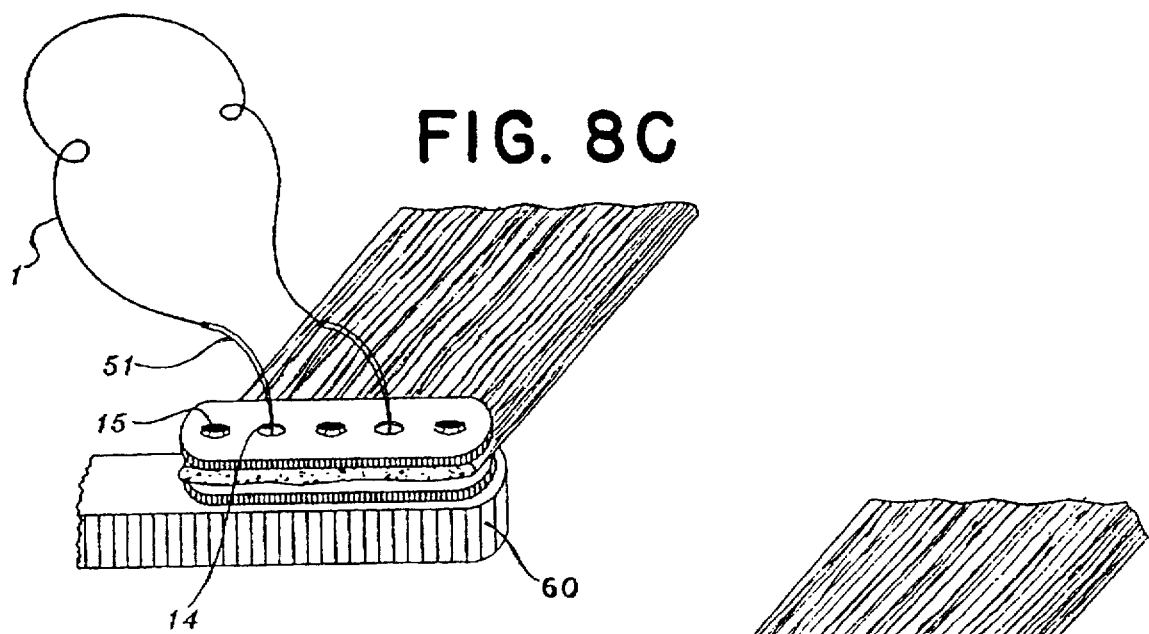
FIG. 8C is an illustration of the assembly after cutting the projecting portion coming up above the top of the upper fixing body, and passing suture and needle through the penetrating holes.

In this state, as illustrated in FIG. 8C, the projecting portion 25 coming up above the upper fixing body 11 is cut on a level with the top of the upper fixing body by using a cutting tool which is not illustrated. Here, the circumference of the cutting plate becomes crushed, thereby pressing the top of the upper fixing body like a rivet. As a result, the upper and lower fixing bodies are resecured more firmly; then, after putting in the needle 51 connected to both ends of suture 1 by half through the penetrating hole 14, 24 for inserting suture, the lower fixing body 21 is detached from the lower supporting body 41. At this time, to put in the needle more deeply, the penetrating hole for inserting suture can be constructed at the place opposite to the penetrating hole 24 for inserting suture of the lower fixing body on the lower supporting body.

Also, the muscle is cut at this stage in case operation is performed as it is raised without cutting it.

Figure 8D:
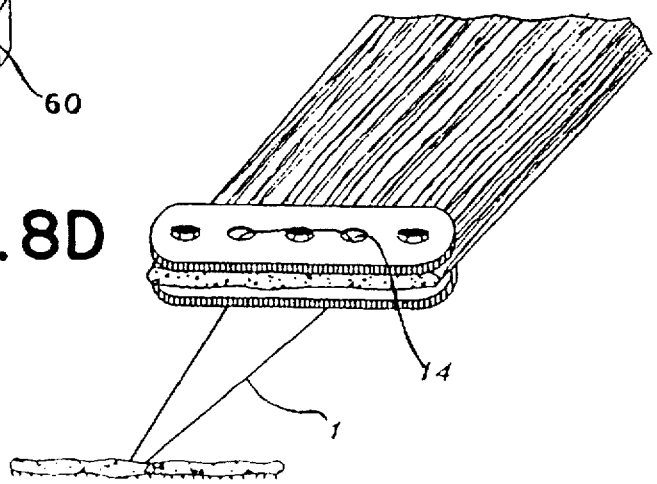
FIG. 8D is an illustration of the assembly after making the suture hang loose and take backwards as much as needed, and attaching the assembly to the original muscle-attached portion of the eyeball.

Next, as illustrated in FIG. 8D, the needle is completely passed in while suture passes in both the penetrating hole 14 of the upper fixing body and the penetrating hole 24 of the lower fixing body. And in this state, after the needle is passed in at the original muscle-attached portion of the eyeball, letting suture hang loose, and then taking backward as much as amount in need.

FIG. 9 illustrates a variation of the lower fixing body 21c of the invention.

As illustrated, the lower fixing body is constructed as a single body with membrane 27. Membrane 27 is 0.02 mm thick in general, thinner than the base part of the lower fixing body, made of polymer, the same material as the lower fixing body 21c. In case membrane is used, the bottom surface of the lower fixing body can be adhered directly to the sclera without using suture, instead using tissue adhesive. In case of this method, since thin membrane is used, the feeling of an alien substance is not much, and adhesion can be easy; and also, because of enlarging the adhesive area, total strength by adhesion can be increased and reliability of operation can be enhanced. Also, the method of operation is simplified because there is no need to adjust the length of suture.

FIG. 9A is another variation of the lower fixing body having membrane. On membrane 27d, a plurality of penetrating holes 28 for inserting suture are made up in set distance, and the marginal spot of the said penetrating hole forms the platform-elevated part 29, a raised place like a hump.

In case of operation by using membrane 27d only, the method of operation is simplified, but it is difficult to adjust exact length, so suture can be used together. At this time, distance can be adjusted by using the penetrating holes 28 for inserting suture. That is, since the said penetrating holes are made up at a preset distance, they can take a role of ruler, so that they can simply adjust distance by inserting suture into the penetrating hole in applicable distance.

Also, the platform-elevated part 29 is set up approximately equivalent to the thickness of the base part of the lower fixing body, and as suture is put into the penetrating hole, platform-elevated part prevents membrane 27 from tearing by suture.

After suture is inserted into the applicable penetrating hole 28, needless remaining membrane 27d beyond the location of the penetrating hole 28 is cut off, and the needle is passed through the center point of stump of muscle insertion, and tied.

Like this, this invention can eliminate side-effects like the piercing of the eyeball which can occur in case needle and suture are used, and manipulation is simple, and in case suture is used, it eliminates such a disadvantage that the width of the muscle is getting narrow according to tension of suture, keeping the primary level form of the muscle up as it is.

The clinical experiment results of operation to which this invention applies will be described as follows.

THE CASE OF THE FIRST EXPERIMENT

For 13 colored tame rabbits of 2–3 kg, after the conjunctiva was exposed, the muscle was fixed to the superior and inferior rectus muscles by using the supporting body and the fixing body of the invention.

Subsequently, the adhesive portion of the superior rectus muscle is cut off by Westcott Scissors, and then in the rear of 3 mm, it is attached to the sclera by using BERIPLAST® (it is called recession), a tissue adhesive. Pulling tests have been carried out in 30 min., one week, two week, four week, eight week, respectively, gaining the results of measuring adhesive strength as follows:

| | 30 min | one week | two week | four week | eight week |
|---|---|---|---|---|---|
| adhesive strength | 110 g | 210 g | 300 g | 480 g | 650 g |

Hence, adhesion proves firmly secured. As for the inferior rectus muscle, the results of examining adhesive width and tissue indicate that the width of the muscle is well maintained, and a slight degree of inflammation reaction occurs, but it declines slowly as one week, two week, four week, and eight week proceed on. Also, fibrosis increases, and in eight week, fibrin is developed between the muscle and the sclera, firmly attaching one and the other.

THE CASE OF THE SECOND EXPERIMENT

For 13 colored tame rabbits of 2–3 kg, after fixing the muscle to the superior and inferior muscles by using the fixing body and the supporting body of the invention, and after taking it backward in the rear of 3 mm out of the muscle-adhesive spot by using the method of the hang-loose, as a result of observing the attached muscle in one week, two week, four week, and eight week, it becomes attached equivalent to the width of the primary muscle.

THE CASE OF THE THIRD EXPERIMENT

With 20 healthy colored tame rabbits under general anesthesia, the conjunctiva of the ocular dexter(the right eye) is first incised, and the superior rectus muscle is detached as well. Then, the superior rectus muscle is tied up by 6-0 vinyl suture, and the portion in which the muscle is attached to the eyeball is cut out by Westcott Scissors, marking the sclera in the rear of 3 mm out of the muscle-adhesive spot by calipers while taking care of the sclera not to be pierced. Subsequently, after needle and suture are passed in to the half of the sclera in thickness and depth; suture is bound alp with conventional recession technique; and the conjunctiva is resecured in its primary place.

In the ocular sinister(the left eye), the conjunctiva is equally cut off, the superior rectus muscle gets exposed, fixing the muscle by using the lower fixing body and the upper fixing body of the invention which have membrane, to cut off the portion attached to the eyeball by Westcott Scissors and thereby pass 6-0 vinyl suture, connecting it to end of membrane, and at the spot attached to the said muscular sclera, the muscle is cut out, and out of which the center of the stump remaining is cut out by needle to be thereby fixed.

In 30 min, one week-, two week, four week, and eight week after operation, the degree of conjunctiva hemorrhage and complications are examined. And after each of the superior rectus muscles of the right and left eyes(the right eye refers to the group using conventional type of hang-loose; the left eye to experimental group) lets exposed under general anesthesia, a Pulling examination is performed.

| | 30 min | one week | two week | four week | eight week |
|---|---|---|---|---|---|
| adhesive strength | | | | | |
| the right eye | 190 g | 310 g | 360 g | 480 g | 650 g |
| the left eye | 210 g | 310 g | 370 g | 490 g | 650 g |

As a result, hemorrhage degree appears slight, and there appears no difference between both eyes.

While preferred embodiment of the present invention have been illustrated in detail, it should be apparent to those with skill in the art that modifications and improvements may be made to the invention without departing from the spirit and scope of the invention as described in the following claims.

What is claimed is:

1. An ocular muscle clamping device for maintaining ocular muscles at a predetermined width, comprising:
    a first bioabsorbable fixing device which includes a plurality of fixing projections formed on one surface of the first fixing device at regular intervals, each projection having a circular cone shape and a sharp end and a plurality of grooves formed on the opposite surface of the first fixing device corresponding to said fixing projections; and
    a second bioabsorbable fixing device which includes a plurality of fixing opening holes each having a first diameter on the surface facing said fixing projections and a second diameter on its opposite surface, said holes formed at regular intervals so as to correspond to said fixing projections,
        wherein the inner surface of said fixing opening holes formed by said first and second diameters has a taper angle constructed and designed to satisfy a self-locking condition with said fixing projection when said projection is forcibly engaged in said hole; and
        wherein the shape and ends of said fixing projections of said first fixing device comprise piercing means to pierce the ocular muscles positioned between the first and second fixing device and said projections become fixed into the fixing opening holes of said second fixing device, thereby fixing the ocular muscles to said clamping device.

2. The device of claim 1, further comprising a bioabsorbable adhesive membrane united with said first fixing device, said membrane having a predetermined width and length.

3. The device of claim 2, wherein said plurality of fixing projections are disposed in a line along said predetermined width, and said membrane further comprising a plurality of penetrating holes for inserting a plurality of sutures at regular intervals along the central axis of longitudinal direction of said membrane.

4. The device of claim 2, wherein said membrane has a thickness of 0.02 millimeters.

5. The device of claim 1 further comprising a thin bioabsorbable membrane having a width at one end corresponding to the width of the muscles fixed to said first fixing device and united with said first fixing device at said one end, said membrane having a length extending away from said projections, said membrane operable to be penetrated by sutures for attaching said fixed muscles pierced by said projections to another muscle without narrowing the width of said fixed muscles, said membrane being of a material which is capable of being cut by surgical scissors.

6. The device of claim 1, wherein said plurality of projections provide gaps between the projections of said first fixing device and said plurality of holes provide gaps between the opening holes of said second fixing device, said devices including a plurality of registering holes in said gaps for inserting the sutures through said first and second fixing devices when engaged.

7. The device of claim 1, wherein said clamping device includes:
    a first supporting device having a plurality of supporting projections on one surface registering with and adapted to be inserted into the grooves of said first fixing device; and a second supporting device having a recess formed on a surface into which said second fixing device is inserted and fixed, and opening holes for penetrating which are formed at places corresponding to said fixing projections of said first fixing device from the bottom of the recess; and pressing means adapted to be connected to said first and second supporting devices to forcibly engage said first and second supporting devices.

* * * * *

UNITED STATES PATENT AND TRADEMARK OFFICE
CERTIFICATE OF CORRECTION

PATENT NO. : 5,797,932  
DATED : August 25, 1998  
INVENTOR(S) : Byung-Moo Mim et al.

Page 1 of 2

It is certified that error appears in the above-identified patent and that said Letters Patent is hereby corrected as shown below:

ON THE TITLE PAGE:

Item --[75] Inventors: Byung-Moo Min; Joon Mook Yang; Nam Sook Cho, all of Daejon-city, Rep. of Korea--;

--[73] Assignee: Jong-Deok Park, Daejon-city, Rep. of Korea--;

Enter the Foreign Application Priority data as follows:

--[30] Foreign Application Priority Data

November 24, 1995  [KR] Korea ................95-43460--;

Col. 1, line 4, delete "muscle more" and insert --muscle surgery. More--;

Col. 3, line 5, delete "has";
      line 59, change "$a$" --a--;

Col. 4, line 8, after "been" insert --shown--;
      line 61, change "body" to --body;--;
      line 67, after "part" insert --32.--;

Col. 5, line 2, after "either" insert --of the--;
      line 6, delete "once" and insert --and--;

UNITED STATES PATENT AND TRADEMARK OFFICE
CERTIFICATE OF CORRECTION

PATENT NO. : 5,797,932
DATED : August 25, 1998
INVENTOR(S) : Byung-Moo Mim et al.

It is certified that error appears in the above-identified patent and that said Letters Patent is hereby corrected as shown below:

Col. 7, line 38, "alp" should be --up--.

Signed and Sealed this

Twenty-third Day of February, 1999

Attest:

Q. TODD DICKINSON

Attesting Officer

Acting Commissioner of Patents and Trademarks